United States Patent [19]

Singh

[11] Patent Number: 4,619,264

[45] Date of Patent: Oct. 28, 1986

[54] METHOD AND APPARATUS FOR TREATMENT OF FRESH FRACTURES, DELAYED UNIONS AND NON-UNIONS OF LIVING BONE

[76] Inventor: Om P. Singh, 62, Chhitwapur Road, Lucknow-226001, U.P., India

[21] Appl. No.: 620,748

[22] Filed: Jun. 14, 1984

[51] Int. Cl.$^4$ .............................................. A61N 1/32
[52] U.S. Cl. .................................................. 128/419 F
[58] Field of Search ............... 128/419 F, 419 R, 421, 128/422

[56] References Cited

U.S. PATENT DOCUMENTS

| | | | |
|---|---|---|---|
| 3,893,462 | 7/1975 | Manning | 128/419 F |
| 4,432,361 | 2/1984 | Christensen et al. | 128/419 F |
| 4,491,128 | 1/1985 | Haschke | 128/419 F |

FOREIGN PATENT DOCUMENTS 605621  5/1978  U.S.S.R. .......................... 128/419 F

Primary Examiner—William E. Kamm
Attorney, Agent, or Firm—Hopgood, Calimafde, Kalil, Blaustein & Judlowe

[57] ABSTRACT

A method and apparatus whereby a direct current at an average amplitude of substantially 20 microamperes is caused to flow from the inserted end of a cathode electrode at one longitudinal side of a fractured or otherwise defective osteal zone, through said zone, and to an anode having electrically conductive circumferential contact with the skin on the other longitudinal side of the zone of the defect. The cathode electrode is a pin inserted through marrow and into internal contact with the cortex at said one longitudinal side. For greatest effectiveness, the direct current comprises a steady component which exceeds the maximum amplitude of a varying component, and both components are of the same polarity.

25 Claims, 5 Drawing Figures

METHOD AND APPARATUS FOR TREATMENT OF FRESH FRACTURES, DELAYED UNIONS AND NON-UNIONS OF LIVING BONE

BACKGROUND OF THE INVENTION

The invention relates to the use of direct current as an aid in healing of defects such as fractures, delayed unions and non-unions in living bone.

Conventional practice for fresh fractures, such as a simple or compound fracture of the tibia, is to apply a long cast and to hope for normal healing within the cast. For a weight-bearing member such as the tibia, the cast may be on the patient for four to six months. Upon removal of the cast, a delayed-union or non-union condition is frequently encountered; and in such event standard practice is to proceed with various options, including bone graft, open reduction and internal fixation (plate and screws), and/or exposure to pulsed electromagnetic fields, as described for example in Ryaby et al. U.S. Pat. No. 4,105,017. For tibia fractures, the number of cases which become delayed-union or non-union cases is at least 30 percent.

Various inventors have addressed the possibility of bone healing through use of direct current. Among these, Brighton et al. U.S. Pat. No. 3,842,841 discloses use of a constant direct current, continuously applied to the region of a fracture or bone defect via a cathode-wire implantation and an anode taped to the skin near the cathode implantation site, wherein constant current is maintained within the range of 5 to 20 microamperes. Levy U.S. Pat. No. 4,026,304 has an extensive discussion of prior art and discloses use of a train of electrical pulses, rather than a direct-current potential, applied to spaced points of an afflicted-bone region via separate wire implantations; the Levy invention was based on various experiments with dogs, involving much surgical invasion. Chiarenza et al. U.S. Pat. No. 4,175,565 discloses an electroconductive dental implant as the cathode for direct-current therapy, wherein the direct current is continuous for relatively short periods not exceeding one hour. And Greatbatch U.S. Pat. Nos. 4,313,438 and 4,314,554 disclose apparatus implanted in the body of a patient for applying direct current in an alternating succession of reversing polarity, to promote germicidal action with one polarity for a period of time, in alternation with promotion of osteogenic action in a succeeding period of opposite polarity.

I have discovered that a high probability of success applies for continuous use of direct current, alone or as a major signal component, in the treatment of fresh fractures of human bone, such as the tibia, and that substantial acceleration of the healing process can occur when direct-current pulses of specifically characterized nature are additively combined with a steady base component of direct current through the site of the fresh fracture.

BRIEF STATEMENT OF THE INVENTION

It is an object of the invention to provide an improved method and means for treatment of conditions of fracture, delayed union, non-union and the like in living bone.

It is a specific object to provide a method and means applicable to fresh fractures for significantly reducing the time required for healing.

Another specific object is to provide a method and means whereby delayed union and non-union consequences can be virtually eliminated in the treatment of fresh fracture in living bone.

It is also an object to achieve the above objects with a treatment method and means whereby infection can be eliminated, and where onset of infection can be avoided, even in the case of compound fractures.

It is a general object to meet the above objects at inherently low cost and as an out-patient clinical procedure with no need for hospitalization.

The invention achieves the foregoing objects with a method and apparatus whereby a direct current at an average amplitude of substantially 20 microamperes is caused to flow from the inserted end of a cathode electrode at one longitudinal side of a fractured or otherwise defective osteal zone, through said zone, and to an anode having electrically conductive circumferential contact with the skin on the other longitudinal side of the zone of the defect. The cathode electrode is a pin inserted through marrow and into internal contact with the cortex at said one longitudinal side. For greatest effectiveness, the direct current comprises a steady component which exceeds the maximum amplitude of a varying component, and both components are of the same polarity.

DETAILED DESCRIPTION

The invention will be described for illustrative examples in conjunction with the accompanying drawings, in which.

Figure 1:
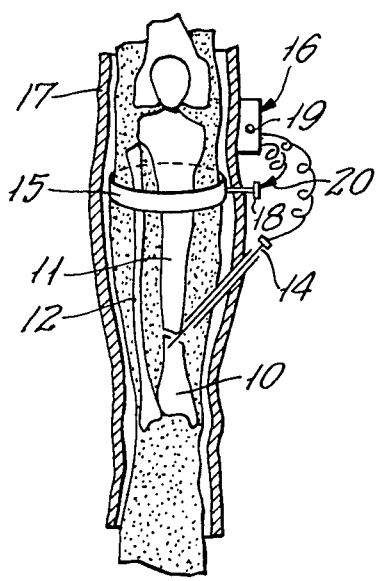
FIG. 1 is a simplified view in partial section to show a fractured tibia and adjacent portions of a human leg, fitted for treatment in accordance with the invention.

In the human leg depicted in FIG. 1, the tibia has suffered fracture within the lower half, thus establishing a shorter distal end 10 and a longer proximal end 11. The fibula 12 has not been affected. The fracture may be viewed as fresh, meaning that it has occurred so recently as to have received no treatment other than first aid, or the fracture may be viewed as a delayed union or non-union by reason of inadequate natural healing capability after a conventional period of cast support.

The apparatus involved in use of the invention comprises an electrically conductive stiff pin or cathode electrode 14, an electrically conductive flexible strap or anode electrode 15, and a self-contained signal generator 16, suitably miniaturized and of such capacity as to serve the needs of continuous therapy for a period of up to eight weeks while taped to the patient's cast, which in FIG. 1 is shown as a conventional plaster cast 17 of the "long" or above-knee variety.

In practice, the afflicted region is initially locally anesthetized, and a cathode 14 is selected, of length more than sufficient for the completed procedure. For this, a stiff stainless-steel Kirschner or "K" wire of 1.5 to 2.5-mm diameter is most satisfactory and is preferred. Wire 14 is pointed and lends itself to self-penetrating entry into the flesh and preferably through the fracture into marrow. As shown in FIG. 1, a biased or sloping entry (i.e., inclined to the longitudinal axis of the bone)

is selected appropriate to the nature and orientation of the fracture and so as to permit driving the inserted end of cathode 14 into burying internal contact with the cortex of the distal end 10, leaving a considerable portion of cathode 14 projecting externally. The anode 15 may be a strip of aluminum foil and is applied over electrically conductive jelly around an upper locale of the proximal end 11; anode 15 is preferably sufficiently flexible to be self-adherent to the skin via the jelly, and it is sufficiently long to permit full circumferential wrap of the region of contact with the skin. Anode 15 is also long enough or is suitably fitted with a conductive lead, whereby the positive-polarity output connection of signal generator 16 may be made thereto. As shown, a terminal stud 18 is a component part of the anode strap 15, and it is adapted to project externally of the cast 17.

Having applied both electrodes 12 and 14, a long plaster or other conventional cast 17 is then applied to the leg. In the case of a plaster cast, both electrodes and their externally projecting portions become stabilized by embedment in cured plaster. The signal generator 16 is then secured to the plaster, as by taping, making sure that its indicator-lamp component 19 (to be described in connection with FIG. 2) is readily visible to the patient. The negative output terminal of generator 16 is connected to cathode wire 14, after the latter has been cut off to relatively short (e.g., 0.5 to 1 cm) exposure outside the cast, and the positive output terminal of generator 16 may be similarly connected to anode 15 via stud 18. Preferably, at least one of these connections is selectively removable by the patient for a testing purpose to be described, and an aligator clip for the purpose is suggested at 20 in FIG. 1.

It is the nature of the above-described procedure that merely by completing the electrical connections to electrodes 14 and 15, the treatment of the invention has already begun, in that signal generator 16 is in readiness to deliver current as soon as its output connections are made to include the anticipated load of body resistance between the electrodes. For a fractured tibia situation, this load has been taken to be in the range of 1K to 10K ohms, throughout the course of continuous electrical therapy.

The patient can appear for weekly X-ray examination after three weeks of treatment in the cast, and most patients are found to have knitted (healed) their fracture sufficiently within 4 to 8 weeks in the cast. When the examining physician concludes that there has been sufficient knitting, the cast and electrodes are removed, and the leg is placed in a patellar tendon bearing brace. After four weeks in the brace, he is relieved of the brace and can return to full weight-bearing use of his leg.

Figure 3:
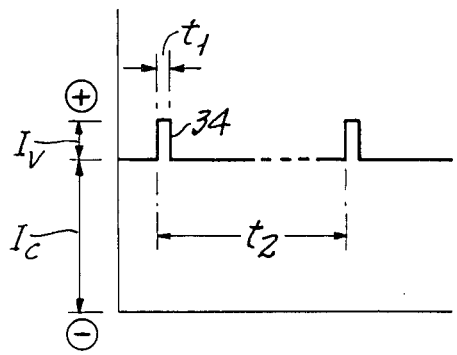
FIG. 3 is a graph to depict a preferred pattern of current involved in treatment as in FIG. 1.
Figure 2:
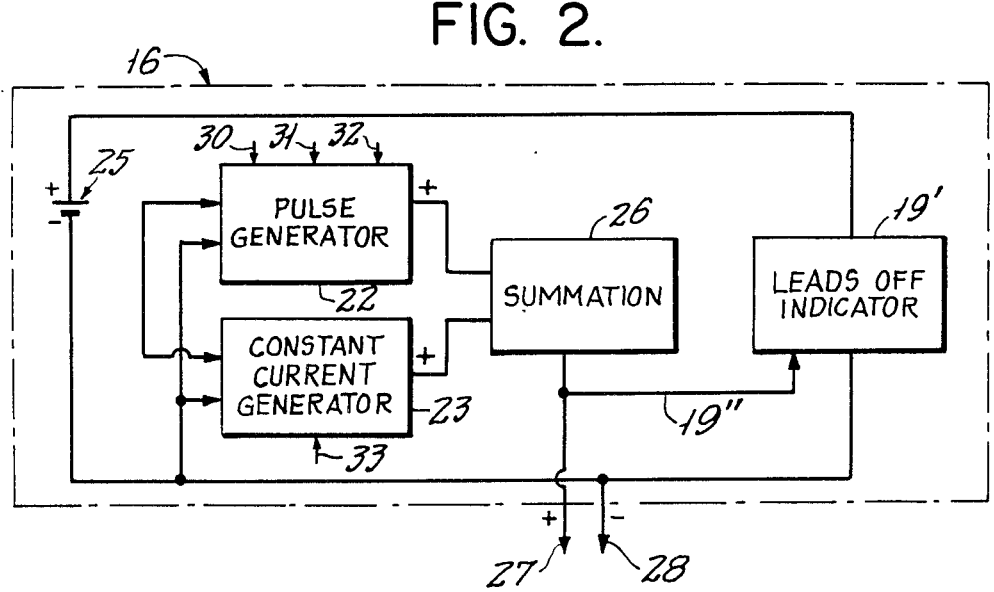
FIG. 2 is an electrical block diagram schematically showing components of the self-contained signal generator of FIG. 1.

Referring to FIGS. 2 and 3, the signal generator 16 is seen to contain a pulse generator 22 and a constant-current generator 23, both of which derive power from a self-contained battery 25, suitably a conventional 9-volt battery. Outputs of generators 22-23 are taken with the same polarity to permit summation at 26, thus providing one of the output terminals 27, here shown as positive, for connection to anode 15, at 18-20. The other output terminal 28 is taken as the negative side of the battery. It is preferred that signal-generator unit 16 be a package, suitably potted, and having no external control of signal magnitude or characterization. However, FIG. 2 will be understood to indicate that prior to potting, the unit 16 may include separate provision for independent adjustment of the output of pulse generator 22, at 30-31-32, in respect of pulse width, pulse-repetition rate, and pulse amplitude, respectively; similarly, the setting of current output of generator 23 into the anticipated resistive load is suggested at 33.

Finally, a "leads-off" indicator 19' will be understood to include visible display, via an externally viewable light-emitting diode at 19 (see FIG. 1); thus, the circuit 19' for such display may function to operate lamp 19 from excitation by battery 25 in the circumstance when a control connection 19" to output lead 27 encounters an open-circuit condition, meaning that the anticipated body resistance is not completing the circuit between terminals 27-28. The patient is normally unconcerned by the fact that lamp 19 is normally extinguished, but he is instructed to periodically check on the sufficiency of his self-contained battery, by momentarily removing clip 20 to open the circuit. If lamp 19 goes "on", his battery is sufficient, and he can assuredly resume treatment by reestablishing the clip connection; but if it does not go "on", then he is instructed to have his doctor apply a new generator unit 16.

In my work to date, I have found best results on tibia fractures when the amplitude of the steady component $I_c$ of current from generator 23 is maintained at substantially 20 microamperes, and when the maximum amplitude is substantially 5 microamperes for the varying current component $I_v$ attributable to the output of pulse generator 22. I have also found a generally square or quasi-rectangular wave shape to be suitable and therefore preferable for the individual pulses 34 of this output. Pulses 34 thus may be described as having steep leading and trailing edges, with a dwell of duration $t_1$ therebetween, and they are repeated at intervals $t_2$. The pulse-duty cycle should be in the range 1:2 to 1:100, and pulse repetition should be in the range of about 20 per second to about 20 per minute; and I have found highly satisfactory results for a pulse-duty cycle of 1:10, where the pulse width is 0.1 second and the time $t_2$ between pulses is 1 second. More generally speaking, the steady base component of current through the afflicted body region is preferably in the range 15 to 25 microamperes, and the maximum amplitude of the pulse or varying component $I_v$ is 4 to 6 microamperes, for a combined maximum of substantially 30 microamperes, and a combined minimum of substantially 20 microamperes. In support of these ranges, I can make the statement based on work to date that a level of 40 microamperes is counterproductive, in that it has been identified with tissue degeneration, and that at 15 microamperes osteogenesis is significantly less effective than at 20 microamperes.

Clinical use supports advantages of the invention, in two independent studies (a) for a series of fresh-fracture tibia cases and (b) for a series of delayed-union and non-union cases. The first of these is reportable at this time and will therefore be described below; the second series has been showing highly satisfactory results and can be fully reported in the near future.

The fresh-fracture study involved treatment of 160 tibial fractures in adults between 16 and 70 years of age and sustaining their fractures within the 24 hours preceding commencement of treatment. The study was carried out to assess the efficacy of different closed methods of treatment of tibial fractures. These 160 patients were divided into four groups, as follows:

A. Fifty patients treated only by manipulative reduction and immobilization in an above-knee plaster cast;

B. Fifty patients treated as in A above for three weeks, followed by patellar tendon bearing bracing;

C. Thirty patients treated by manipulative reduction, immobilization in an above-knee plaster cast, and electric stimulation at the fracture site as described for FIG. 1 except that the excitation was a steady direct current; and D. Thirty patients treated as in C above, except that the electric stimulation involved the addition of pulses as described in connection with FIGS. 2 and 3.

For groups C and D above, the average period of electric stimulation was six weeks, followed by a patellar tendon bearing brace.

Figure 4:
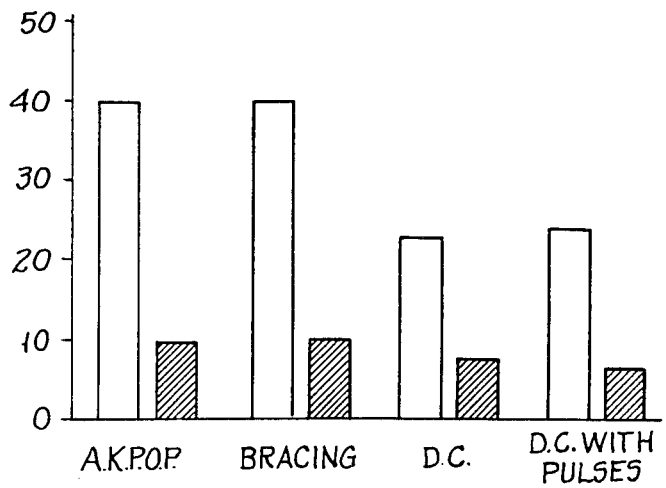
FIGS. 4 and 5 are bar charts in illustration of the statistical distribution of patients involved in results reported below.
Figure 5:
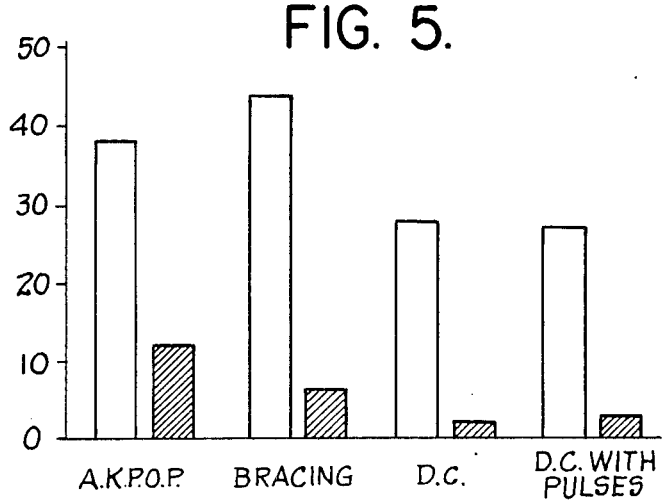

FIG. 4 is a bar graph to show by sex the number of patients in each treated group. In this graph, the successive labels "A.K.P.O.P.", "Bracing", "Direct current", and "Direct current with pulses", respectively, correspond to the different categories of treatment outlined for groups A, B, C, D above. The same labeling also applies for the bar graph of FIG. 5 wherein the distribution of simple vs. compound fractures is presented. And the same labeling also applies for the following tabulation to show the distribution of fracture location, for number of patients in each group:

| Group A A.K.P.O.P. | Group B Bracing | Fracture Location in Tibia | Group C D.C. | Group D D.C. + Pulses |
|---|---|---|---|---|
| 4 | 8 | Upper Third | 5 | 5 |
| 30 | 18 | Middle Third | 12 | 6 |
| 16 | 24 | Lower Third | 13 | 19 |

The same labeling further applies for the following tabulation to show, by number of persons, the classification of fractures according to radiographic type:

| Group A A.K.P.O.P. | Group B Bracing | Radiographic Type | Group C D.C. | Group D D.C. + Pulses |
|---|---|---|---|---|
| 8 | 10 | Transverse | 6 | 6 |
| 22 | 22 | Longitudinal | 11 | 11 |
| 20 | 18 | Comminuted | 13 | 13 |

The patients of Groups A and B above were initially treated by surgical toilet and closure, before their fractures were reduced and immobilized. The 50 patients of Group A were kept in above-knee plaster until union occurred, and the 50 of Group B were in above-knee plaster for three weeks, followed by bracing until union occurred. These 100 patients formed a control group for comparison with the 60 patients of Groups C and D who received electrical stimulation, using a Kirschner-wire cathode inserted percutaneously at the fracture site in contact with the proximal part of the distal fragment. Following an average period of six weeks of electrical stimulation, the above-knee plasters and electrodes were replaced by bracing until union was clinically and radiographically sound. In all cases, union was considered complete when there was no abnormal movement or tenderness at the fracture site, and callus was apparent on the radiograph. All fractures were clinically and radiographically examined at four, six and eight weeks thereafter, as clinically indicated.

|  | AVERAGE | RANGE Minimum | RANGE Maximum |
|---|---|---|---|
| Group A (A.K.P.O.P.) | 22.8 weeks | 17.5 weeks | 24.6 weeks |
| Group B (Bracing) | 18.84 weeks | 14.4 weeks | 21.3 weeks |
| Group C (D.C.) | 13.67 weeks | 10.3 weeks | 15.2 weeks |
| Group D (D.C. + Pulses) | 10.70 weeks | 8.1 weeks | 12.3 weeks |

As a general observation, it was clear that both Groups C and D (treated by electrical stimulation) healed significantly more rapidly ($p<0.001$) than the two control groups (A and B). As between Groups A and B, those treated with a patellar tendon bearing cast brace healed significantly more rapidly ($p<0.001$) than those treated with an above-knee plaster alone; for Group B, the mean time to union was 18.8 weeks (range 14.4 to 21.3 weeks), compared to 22.8 weeks (range 17.5 to 24.6 weeks) for Group A. And the time to union in the 30 fractures of Group D (stimulated by direct current plus pulses) was significantly shorter ($p<0.001$) than for the 30 fractures of Group C (stimulated by direct current alone).

One of the 60 patients treated by electrical stimulation developed hypergranulation at the point of cathode entry, and six patients had peeling of skin around the anode area. However, all these lesions healed within one week, without any specific treatment. And there were no significant complications in the control group of patients.

It will be seen that the described invention meets all stated objects, with procedure which is simple, safe and functionally effective. No non-union or bone infection has been observed in use of the invention, even in the case of compound fractures; in fact, the observation has been made that even when electrical stimulation of the invention is applied to an infected region of treatment, the infection is soon eliminated. The above-reported study shows (a) a 36 percent reduction in healing time for constant direct current (Group C) as compared to the control group, and (b) a further 23 percent reduction in healing time for use of constant direct current with superposed pulses (Group D). Even though the invention is invasive, in that a Kirschner wire is inserted percutaneously, this can be done on an out-patient basis and does not require hospitalization.

While the invention has been described in detail for a preferred embodiment, it will be understood that modifications may be made without departing from the scope of the invention. For example, even though Kirschner wire, coated with Teflon to all but an exposed tip at the insertion end, was used in the above-reported study, it has been established that the Teflon coating is not necessary and that results equivalent to those reported for Groups C and D are obtainable with or without Teflon coating. Also, even though cathode insertion has been described as via the fracture itself, this will be understood to be for the reason of simple out-patient use of the invention; for example, in certain cases, it may be desirable to drill a bone fragment to enable a particularly indicated insertional orientation of the cathode pin 14, but the insert is nevertheless still preferably made as indicated above, through the marrow and to the cortex of the involved fragment, or through the bone and involved cortex to at least partial entry into the marrow. Further, although described in connection with a single cathode 14, the single cathode may be one of several cathodes entering into cortex contact with the same bone fragment via plural spaced and differently oriented approaches, all such cathodes being electrically served by the output of the same signal-generator means 16 and by circuit completion via the same anode 15.

It will further be understood that the manner of generating pulsed direct current of the nature described in connection with FIG. 3 may be via various techniques not necessarily involving separate generation of the constant-current component and of the varying-current component in the same polarity. The description and showing in connection with FIG. 2 are therefore highly schematic and may be considered generally illustrative of achieving the same waveform, for example, either through pulse-amplitude modulation of a steady component, or through combination of a positive constant-current component with negatively polarized pulses, the latter being so shaped that pulses 34 of width $t_1$ are attributable to the short period ($t_1$) between relatively long-duration negative pulses of width $t_2-t_1$.

What is claimed is:

1. The method of treating freshly fractured bone in a living body which comprises selecting an electrically conductive pin element and inserting the same through flesh and marrow in the vicinity of the fracture to the extent of lodging the inserted end in internal contact with cortex tissue at one longitudinal side of the site of the fracture, applying an electrically conductive element in conductive contact with flesh in the vicinity of the fracture on the other longitudinal side of the site of the fracture, applying a single longitudinal cast over both sides of the fracture and over the sites of both of said elements with separate electrical connections external to the cast, passing direct durrent through the body via said connections, the polarity of current connection being exclusively such as to establish negative potential at said pin element with respect to positive potential at the other of said elements, the direct current comprising a steady component and a varying component, said varying component being a succession of direct-current pulses of said polarity superposed on said steady component, and maintaining the average amplitude of current via said connections at about 20 microamperes for a period of at least three weeks before removal of the cast and of said elements.

2. The method of claim 1, wherein said pulses are of magnitude which is a fraction of the magnitude of the steady component, and wherein the duty cycle of the succession of pulses is in the range 1:2 to 1:100.

3. The method of claim 2, in which the duty cycle is in the order of 1:10.

4. The method of treating proximal and distal fragments of a living bone, which comprises selecting an electrically conductive pin cathode and inserting the same through flesh and marrow between said fragments to the extent of burying the inserted end in cortex tissue of one of said fragments applying an electrically conductive element as an anode in conductive contact with flesh adjacent the other of said fragments, applying a single longitudinal cast over both fragments with separate electrical anode and cathode connections external to the cast, connecting a source of direct current to said connections, the polarity of current connection being exclusively such as to establish negative potential at said cathode with respect to positive potential at said anode, said direct current comprising a steady component and a varying component, said varying component being a succession of direct-current pulses of said polarity superposed on said steady component, and maintaining the average amplitude of current via said connections within the range of 15 to 30 microamperes for a period of at least three weeks before removal of the cast and of said anode and cathode.

5. The method of claim 4, in which said pulses are of magnitude which is a fraction of the magnitude of the steady component, and in which the duty cycle of the succession of pulses is in the order of 1:10.

6. The method of claim 4, in which the amplitude of said steady component is about 20 microamperes and the maximum level of said varying component is about 5 microamperes.

7. The method of claim 4, in which the amplitude of said steady component is in the range 15 to 25 microamperes and the maximum level of said varying component is in the range 4 to 6 microamperes.

8. The method of claim 7, in which the combined maximum amplitude of said components is at least 20 microamperes.

9. The method of claim 7, in which the combined maximum level of said components does not exceed 30 microamperes.

10. The method of claim 4, in which said pulses are generally rectangular.

11. Apparatus for treating the situs of a defect between proximal and distal portions of a living bone, comprising a pin cathode of stiff electrically conductive material surgically invasively inserted in the region of said defect and into contact with the cortex within one of said portions, an anode in conductive application to flesh adjacent the other of said portions, said pin cathode projecting externally of flesh at the site of pin insertion, and pulse-generator means having an output connected to said anode and cathode for exciting the situs of said defect via said anode and cathode with therapeutically beneficial signals which satisfy the following criteria:

(a) the signals are exclusively characterized by a steady direct-current component wherein the polarity at the cathode is continuously negative with respect to that at the anode;

(b) the signals are further characterized by a pulsing component wherein succeeding pulses of the polarity of said steady component are superposed on said steady component;

(c) the amplitude of said signals is such as to maintain an average current in the order of 20 microamperes via said anode and cathode and electrically connected portions of living bone;

(d) the maximum pulse amplitude is in the range of $\frac{1}{8}$ to 1/6 of the amplitude of the direct-current component; and (e) the duty cycle of the pulse component is in the range 1:2 to 1:100.

12. The apparatus of claim 11, in which the duty cycle is in the order of 1:10.

13. The apparatus of claim 11, in which the amplitude of said signals is such as (a) to maintain in the order of 20 microamperes the level of the steady component and (b) to establish a maximum level in the order of 5 microamperes for pulses of the pulse component.

14. The apparatus of claim 11, in which the amplitude of said signals is such as (a) to maintain the level of the steady component in the range 15 to 25 microamperes and (b) to establish a maximum level of pulses of said pulse component within the range 4 to 6 microamperes.

15. The apparatus of claim 14, in which the combined instantaneous maximum level of said components does not exceed 30 microamperes.

16. The apparatus of claim 14, in which the combined instantaneous maximum level of said components is at least 20 microamperes.

17. The apparatus of claim 11, in which pulses of said pulsing component are generally rectangular.

18. The apparatus of claim 17, in which pulses of said pulsing component are characterized by a relatively steep leading edge and by a dwell preceding a trailing edge.

19. The apparatus of claim 17, in which pulses of said pulsing component are characterized by a relatively steep trailing edge and by a dwell between a leading edge and said trailing edge.

20. The apparatus of claim 11, in which said cathode is a Kirschner wire.

21. The apparatus of claim 11, in which said pulse-generator means is a self-contained unit including a battery and is mounted to an orthopedic cast.

22. Apparatus according to claim 21, in which said unit includes means whereby said pulse-generator means may be selectively placed in open-circuit condition, said unit including an externally visible indicator of instantaneous battery sufficiency when the output of said pulse-generator means is in open-circuit condition.

23. Apparatus according to claim 11, in which rate of the pulse repetition is in the range of about 20 per second to about 20 per minute.

24. Apparatus according to claim 11, in which the rate of pulse repetition is in the order of one per second.

25. In the treatment of fractured bone in a living body by surgically inserting an electrically conductive electrode element into conductive end contact with cortex tissue in the vicinity of the fracture and causing a direct current to flow through said electrode element and into said cortex tissue and nearby flesh and marrow, the improvement comprising maintaining the polarity of current flow exclusively such as to establish at said electrode element a negative potential with respect to nearby flesh and marrow, the direct current comprising a steady component and a varying component, said varying component being a succession of direct-current pulses of said polarity superposed on said steady component, and maintaining the average amplitude of said current flow within the range of 15 to 30 microamperes for a period of at least three weeks.

* * * * *